US012618748B2

(12) United States Patent (10) Patent No.: US 12,618,748 B2
Nair et al. (45) Date of Patent: May 5, 2026

(54) CYLINDER HEAD CRACK DETECTION SYSTEM

(71) Applicant: Progress Rail Locomotive Inc., LaGrange, IL (US)

(72) Inventors: Adarsh G. Nair, Naperville, IL (US); Raji Rexavier, Plainfield, IL (US)

(73) Assignee: Progress Rail Locomotive Inc., LaGrange, IL (US)

( * ) Notice: Subject to any disclaimer, the term of this patent is extended or adjusted under 35 U.S.C. 154(b) by 321 days.

(21) Appl. No.: 18/368,322

(22) Filed: Sep. 14, 2023

(65) Prior Publication Data

US 2025/0093234 A1     Mar. 20, 2025

(51) Int. Cl.
G01M 15/05     (2006.01)
B61L 15/00     (2006.01)
G01N 33/28     (2006.01)

(52) U.S. Cl.
CPC ......... G01M 15/05 (2013.01); B61L 15/0081 (2013.01); G01N 33/2888 (2013.01)

(58) Field of Classification Search
CPC .............. G01M 15/05; B61L 15/0081; G01N 33/2888; B61C 5/00
See application file for complete search history.

(56) References Cited

U.S. PATENT DOCUMENTS

| | | | |
|---|---|---|---|
| 9,303,303 B2 | 4/2016 | Meyer et al. | |
| 10,138,836 B2 | 11/2018 | Zimmer et al. | |
| 2005/0114088 A1 | 5/2005 | Gorden et al. | |
| 2016/0010537 A1* | 1/2016 | Strode .................. | G01M 3/025 |
| | | | 123/41.15 |
| 2017/0363054 A1 | 12/2017 | Pickard | |

FOREIGN PATENT DOCUMENTS

| | | | | | |
|---|---|---|---|---|---|
| KR | 20030018882 A | * | 3/2003 | ............. | G01N 19/08 |
| KR | 100405732 B1 | | 11/2003 | | |
| KR | 100448123 B1 | | 9/2004 | | |

* cited by examiner

*Primary Examiner* — Timothy P Graves

(57)     ABSTRACT

A crack detection system for a cylinder head associated with an internal combustion engine of a locomotive is disclosed. The crack detection system comprises: a closed-loop coolant system for cooling the cylinder head; a sensor assembly including a pressure sensor, and a speed sensor; and a controller in communication with the sensor assembly. The controller is configured to monitor a coolant pressure feedback and an engine duty cycle of the internal combustion engine. The controller is further configured to communicate an alert signal indicative of an existence of a crack in the cylinder head when: coolant pressure signals are greater than or equal to a first threshold and less than a second threshold; a pressure decay is calculated greater than a third threshold.

20 Claims, 8 Drawing Sheets

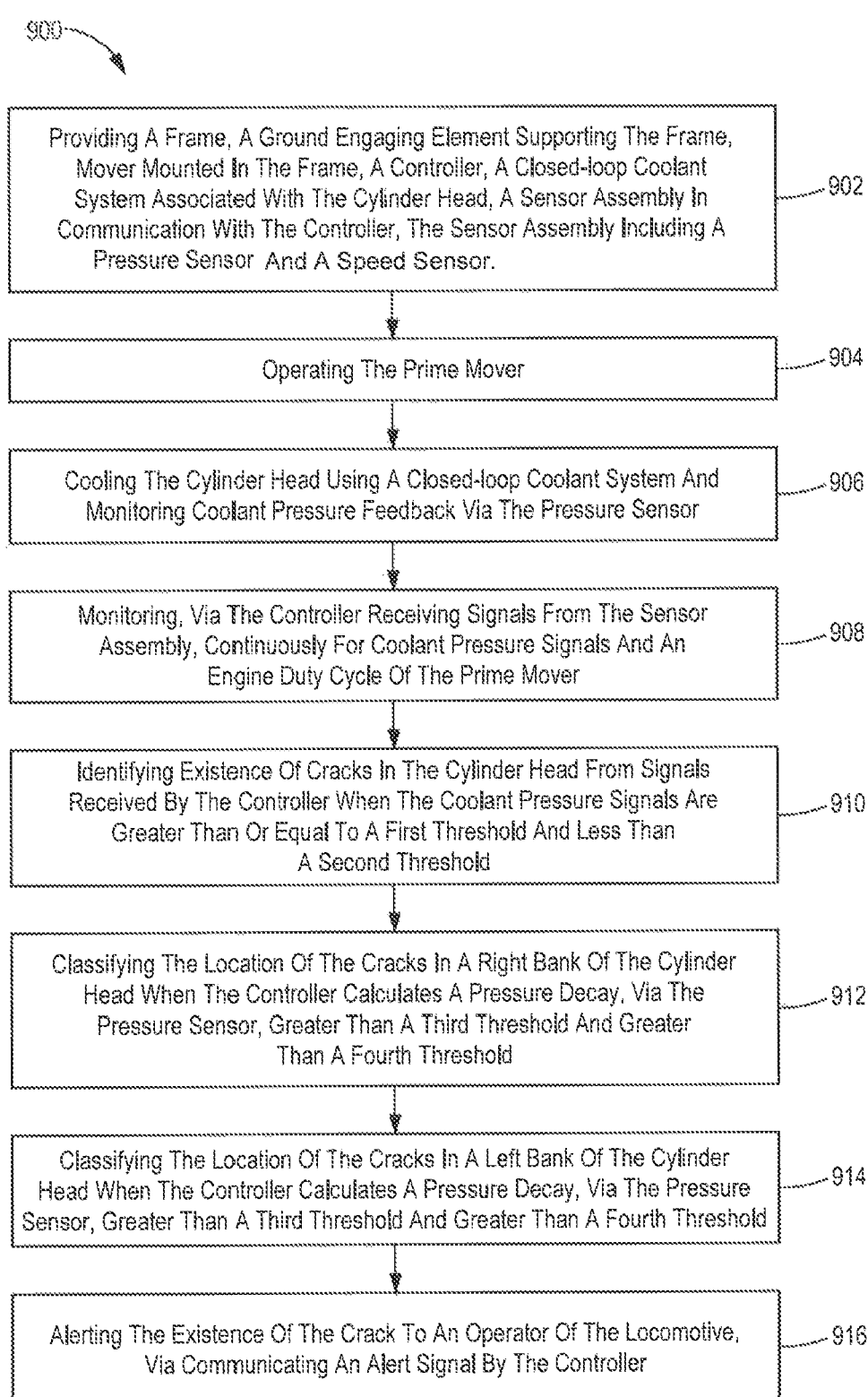

900

Providing A Frame, A Ground Engaging Element Supporting The Frame, Mover Mounted In The Frame, A Controller, A Closed-loop Coolant System Associated With The Cylinder Head, A Sensor Assembly In Communication With The Controller, The Sensor Assembly Including A Pressure Sensor And A Speed Sensor. — 902

Operating The Prime Mover — 904

Cooling The Cylinder Head Using A Closed-loop Coolant System And Monitoring Coolant Pressure Feedback Via The Pressure Sensor — 906

Monitoring, Via The Controller Receiving Signals From The Sensor Assembly, Continuously For Coolant Pressure Signals And An Engine Duty Cycle Of The Prime Mover — 908

Identifying Existence Of Cracks In The Cylinder Head From Signals Received By The Controller When The Coolant Pressure Signals Are Greater Than Or Equal To A First Threshold And Less Than A Second Threshold — 910

Classifying The Location Of The Cracks In A Right Bank Of The Cylinder Head When The Controller Calculates A Pressure Decay, Via The Pressure Sensor, Greater Than A Third Threshold And Greater Than A Fourth Threshold — 912

Classifying The Location Of The Cracks In A Left Bank Of The Cylinder Head When The Controller Calculates A Pressure Decay, Via The Pressure Sensor, Greater Than A Third Threshold And Greater Than A Fourth Threshold — 914

Alerting The Existence Of The Crack To An Operator Of The Locomotive, Via Communicating An Alert Signal By The Controller — 916

FIG. 9

CYLINDER HEAD CRACK DETECTION SYSTEM

TECHNICAL FIELD

The present disclosure generally relates to engines, and more particularly relates to cylinder heads of combustion engines.

BACKGROUND

Engines for transportation machines, such as diesel engines for trains and boats, play a critical role in the transportation industry, powering locomotives and marine vessels that haul heavy loads over long distances. These engines consist of numerous components, including cylinder heads, which are essential for the proper functioning of the combustion chambers and valve mechanisms. Cylinder heads serve as critical sealing elements, facilitating efficient combustion and ensuring the integrity of the engine's internal components.

Detecting the occurrence of cracks in cylinder heads is critical in maintaining the reliability and safety of the engines for operation. Running a locomotive engine with a cracked cylinder head poses significant risks, including coolant leakage, loss of compression, and potential engine overheating, which can lead to engine damage or failure. Continuing to operate a locomotive engine with a cracked cylinder head can result in costly repairs and extended downtime. Timely detection of these cracks is crucial to prevent costly repairs, minimize downtime, and avoid catastrophic failures during operation with existing cracks.

Existing crack detection methods often rely on visual inspections, pressure tests, dye penetrant testing, or non-destructive testing methods such as magnetic particle inspection or ultrasonic testing. While these methods have been utilized to some extent, they suffer from various drawbacks that limit their practicality and reliability to detect small or hidden cracks.

Furthermore, the existing crack detection systems may lack integration and automation, requiring manual coordination between different testing methods and modules. This can lead to inefficiencies, errors, and increased complexity in the crack detection process, hindering the overall reliability and productivity of the rail engine maintenance operations.

Others have attempted to develop a solution for detecting cracks in cylinder heads. For example, in KR100448123, an apparatus is proposed for crack detection during engine endurance tests in vehicles. KR100448123 relies on a constant pressure method in the cooling water passage and connecting pressure measuring hoses attached to the intake and exhaust manifolds. However, this method falls short in accurately identifying crack positions in the cylinder head and is insufficient for comprehensive crack detection.

Hence, there exists a need for a crack detection system that provides enhanced accuracy, efficiency, automation, and integration, enabling early and reliable detection of cracks in cylinder heads while minimizing maintenance costs, and downtime.

SUMMARY

In accordance with one aspect of the disclosure, a crack detection system for a cylinder head associated with an internal combustion engine of a locomotive is disclosed. The crack detection system comprises: a closed-loop coolant system for cooling the cylinder head; a sensor assembly including a pressure sensor and a speed sensor; and a controller in communication with the sensor assembly. The controller is configured to monitor a coolant pressure feedback, an engine duty cycle of the internal combustion engine. The controller is further configured to communicate an alert signal indicative of an existence of a crack in the cylinder head when: coolant pressure signals are greater than or equal to a first threshold and less than a second threshold; a pressure decay is calculated greater than a third threshold.

In accordance with another aspect of the disclosure, a locomotive is disclosed. The locomotive comprises: a frame; a prime mover mounted on the frame; a ground engaging element supporting the frame; a cab; and a crack detection system for a cylinder head associated with the prime mover. The crack detection system includes a closed-loop coolant system for cooling the cylinder head; a sensor assembly including a pressure sensor and a speed sensor; and a controller in communication with the sensor assembly. The controller is configured to monitor a coolant pressure feedback and an engine duty cycle of the internal combustion engine. The controller is further configured to communicate an alert signal indicative of an existence of a crack in the cylinder head when: coolant pressure signals are greater than or equal to a first threshold and less than a second threshold; a pressure decay is calculated greater than a third threshold.

In accordance with another aspect of the disclosure, a method for detecting and classifying cracks in a cylinder head of a locomotive engine in a locomotive. The method comprises the steps of: providing a frame, a ground engaging element supporting the frame, the prime mover mounted in the frame, a controller, a closed-loop coolant system associated with the cylinder head, a sensor assembly in communication with the controller, the sensor assembly including a pressure sensor and a speed sensor; operating the locomotive engine; cooling the cylinder head using a closed-loop coolant system and monitoring the coolant pressure feedback via the pressure sensor; monitoring, via the controller receiving signals from the sensor assembly, continuously for coolant pressure signals, and an engine duty cycle of the prime mover; identifying existence of cracks in the cylinder head from signals received by the controller when the coolant pressure signals are greater than or equal to a first threshold and less than a second threshold; classifying the location of the cracks in a right bank of the cylinder head when the controller calculates a pressure decay, via the pressure sensor, greater than a third threshold and greater than a fourth threshold; classifying the location of the cracks in a left bank of the cylinder head when the controller calculates a pressure decay, via the pressure sensor, greater than a third threshold and less than a fourth threshold; and alerting the existence of the crack to an operator of the locomotive, via communicating an alert signal by the controller.

These and other aspects and features of the present disclosure will be better understood upon reading the following detailed description when read in conjunction with the accompanying drawings.

BRIEF DESCRIPTION OF THE DRAWINGS

FIG. 9 is a flow-chart of a method of detecting cracks in a cylinder head, according to an embodiment of the present disclosure.

Figure 1:
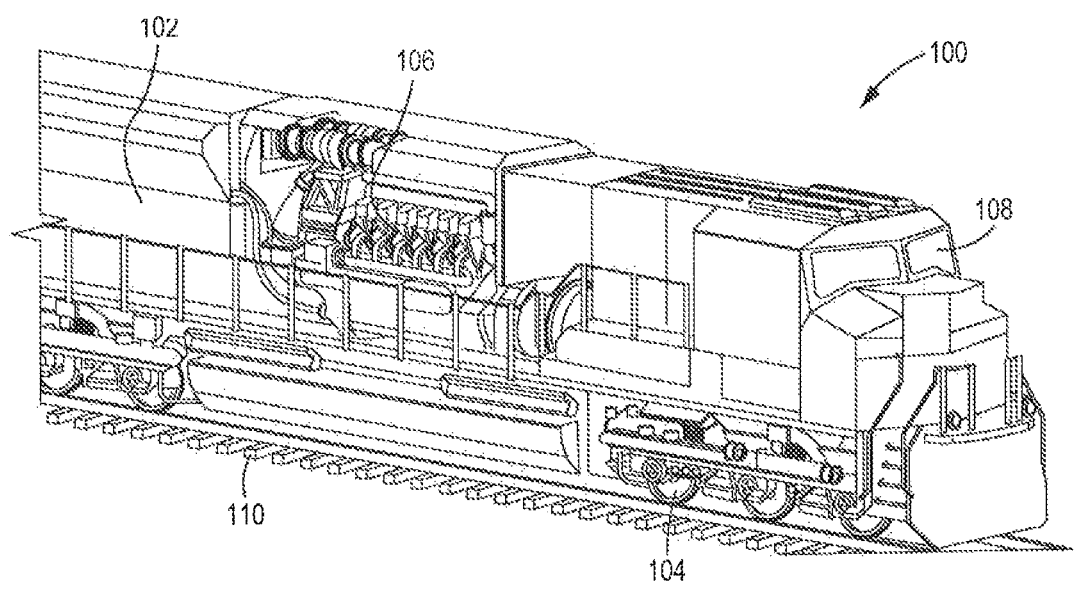
FIG. 1 is a perspective view of a locomotive, according to an embodiment of the present disclosure.

The figures depict one embodiment of the presented disclosure for purposes of illustration only. One skilled in the art will readily recognize from the following discussion that alternative embodiments of the structures and methods illustrated herein may be employed without departing from the principles described herein.

DETAILED DESCRIPTION

Referring now to the drawings, and with specific reference to the depicted example, a locomotive 100 is shown, illustrated as an exemplary train. Locomotives are vehicles designed to transfer goods and materials across railways. While the following detailed description describes an exemplary aspect in connection with the train, it should be appreciated that the description applies equally to the use of the present disclosure in other machines, including, but not limited to, work machines, excavators, boats, backhoes, front-end loaders, shovels, draglines, skid steers, wheel loaders, and tractors, as well.

Referring now to FIG. 1, the locomotive 100 comprises a frame 102. The frame 102 is supported on ground engaging elements 104, illustrated as continuous tracks. It should be contemplated that the ground engaging elements 104 may be any other type of ground engaging elements 104 such as, for example, wheels, etc. The locomotive 100 further includes a prime mover 106 in the frame 102, and a cab 108 for operator personnel to operate the locomotive 100. The prime mover 106 may be an internal combustion engine serving as the primary source of locomotive power, as generally known in the arts. The prime mover 106 may use diesel, gasoline, or other alternate energy sources such as ethanol, ammonia, natural gas, and hydrogen, etc., as fuel.

Figure 2:
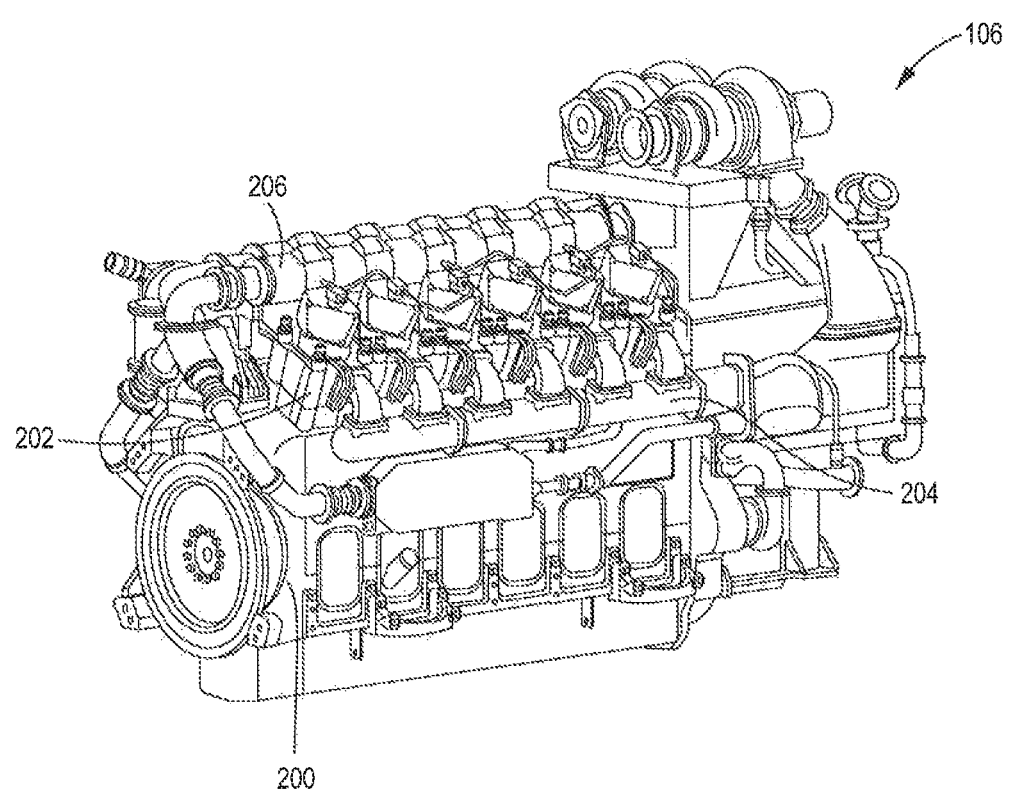
FIG. 2 is a perspective view of a prime mover of the locomotive of FIG. 1, according to an embodiment of the present disclosure.

Now referring to FIG. 2, FIG. 2 illustrates the prime mover 106 as an internal combustion engine, which serves as the primary power source for the locomotive 100, according to one embodiment of the disclosure. The prime mover 106 converts fuel and air into mechanical energy, propelling the locomotive 100 and facilitating its movement along railway tracks 110. The use of an internal combustion engine as the prime mover 106 may provide the locomotive 100 with required necessary power and torque to handle various loads and terrains. The prime mover 106 may be an internal combustion engine such as a diesel engine or an Otto cycle engine, among others.

The prime mover 106 may include an engine block 200, combustion chambers 202, an air intake system 204, and an exhaust system 206. The engine block 200 serves as the foundation of the prime mover 106, housing where the fuel and air mixture undergoes the combustion process. It provides structural integrity and support for various engine components, ensuring the engine's durability and efficient operation. The combustion chambers 202 is where the fuel and air mixture ignites, generating high-pressure gases that exert force on the pistons, converting the thermal energy into mechanical work to drive the ground engaging elements 104 of the locomotive 100. The design and configuration of the combustion chambers 202 may influence the engine's performance characteristics, such as power output, fuel efficiency, and emissions control.

The air intake system 204 and exhaust system 206 work in conjunction to manage the flow of air and exhaust gases within the prime mover 106 to ensure that the prime mover 106 receives a sufficient and controlled amount of air for combustion, while the exhaust system 206 is responsible for expelling emissions, such as carbon dioxide.

Figure 3:
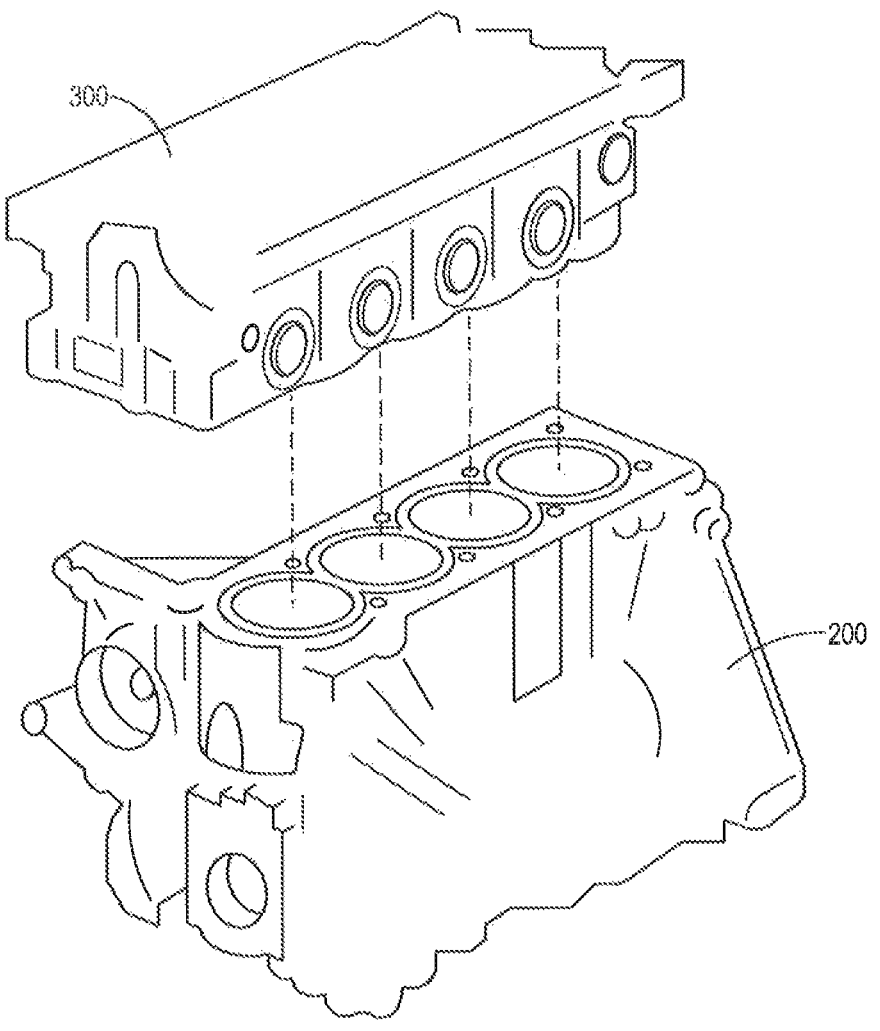
FIG. 3 is a perspective exploded view of an engine block and cylinder head of the prime mover of FIG. 2, according to an embodiment of the present disclosure.

Now referring to FIG. 3, FIG. 3 illustrates an exploded view of an engine block 200 and cylinder head 300 of the prime mover 106 of FIG. 2, according to one embodiment of the disclosure. The engine block 200 and the cylinder head 300 work together to facilitate the combustion process and ensure optimal performance. The engine block 200 may be made from cast iron or aluminum alloy, that houses the cylinders, piston assemblies, and other critical components of the prime mover 106.

The cylinder head 300, forms the uppermost part of the engine block 200 and sits atop the cylinders, sealing the combustion chambers 202 and allowing for the controlled combustion process to occur. The cylinder head 300 may be made from durable materials like cast iron or aluminum alloy with machined surfaces to ensure proper sealing with the engine block 200. A machined surface enables efficient heat transfer and compression within the combustion chambers 202, essential for achieving optimal engine efficiency.

Figure 4:
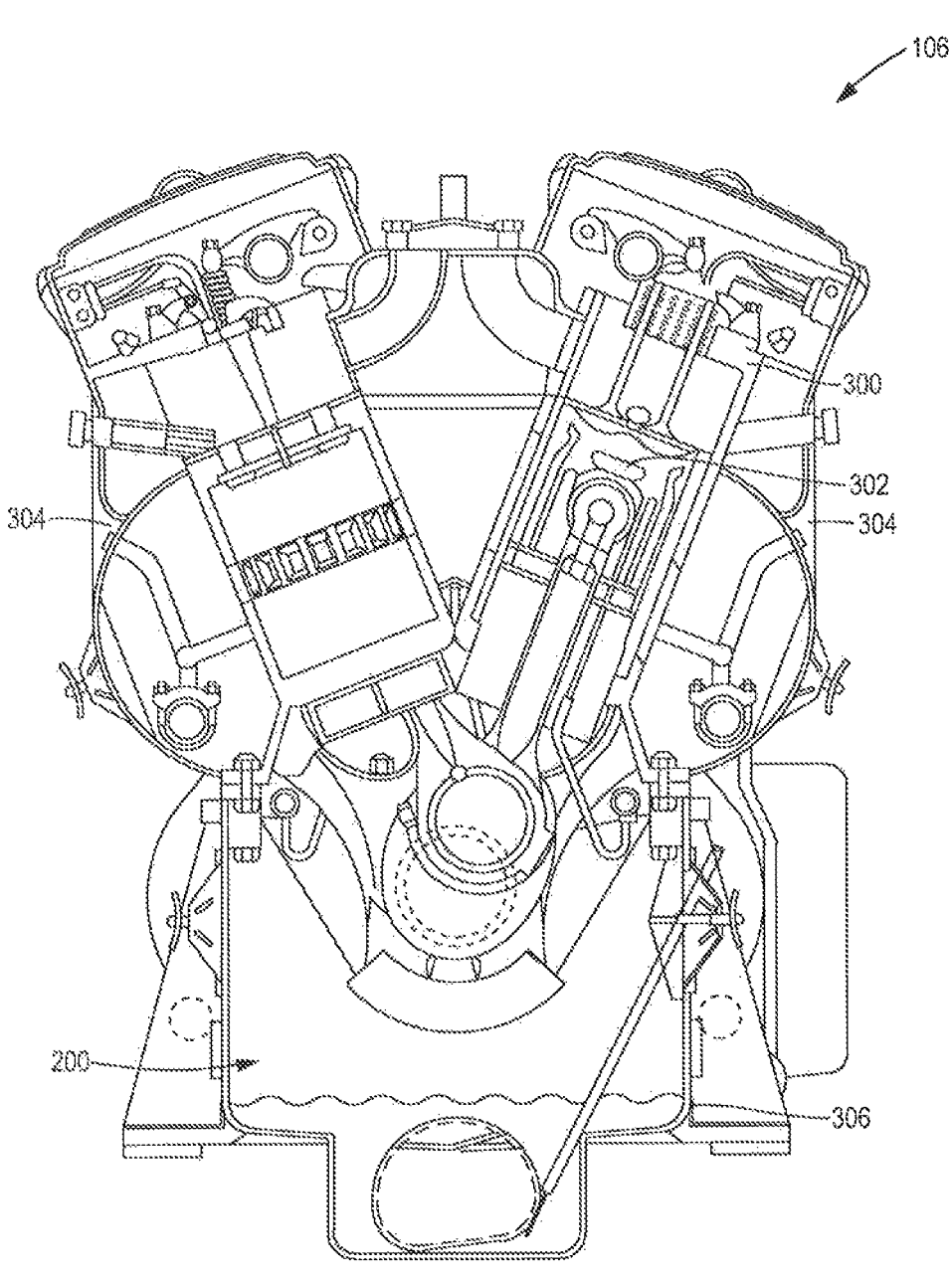
FIG. 4 is a cross-sectional view of the prime mover, according to an embodiment of the present disclosure.

Now referring to FIG. 4, a cross-sectional view of the prime mover 106 is illustrated, according to one embodiment of the disclosure. The cylinder head 300 sits atop the engine block 200 and seals the combustion chambers 202 to facilitate the combustion process and ensure optimal performance of the prime mover 106. As the fuel and air mixture ignites in the combustion chambers 202, the resulting pressure pushes a piston 302 downward, converting the thermal energy into mechanical work that drives the ground engaging elements 104. The prime mover 106 also includes an oil pan 306 to collect oil drops from oil in the prime mover 106.

Within the combustion chambers 202, the mixture of fuel and air ignites, generating high-pressure gases that forcefully push the piston 302 downward. The piston 302 converts the thermal energy derived from the combustion process into mechanical work. As the piston 302 moves downward, the piston 302 produces power to the ground engaging elements 104 for enabling the locomotive 100 to move along the railway tracks 110 or other terrain.

Intake and exhaust valves open and close at intervals during operation and allow the fuel-air mixture to enter the combustion chambers 202 and enable the exhaust gases to exit after combustion. This ignition process initiates a combustion event, leading to the rapid expansion of gases and the generation of the pressure required to drive the piston 302. The cylinder head 300 may house other engine components, such as the intake and exhaust valves, spark plugs, and fuel injectors, which play essential roles in the combustion process, as generally known in the arts.

Figure 5:
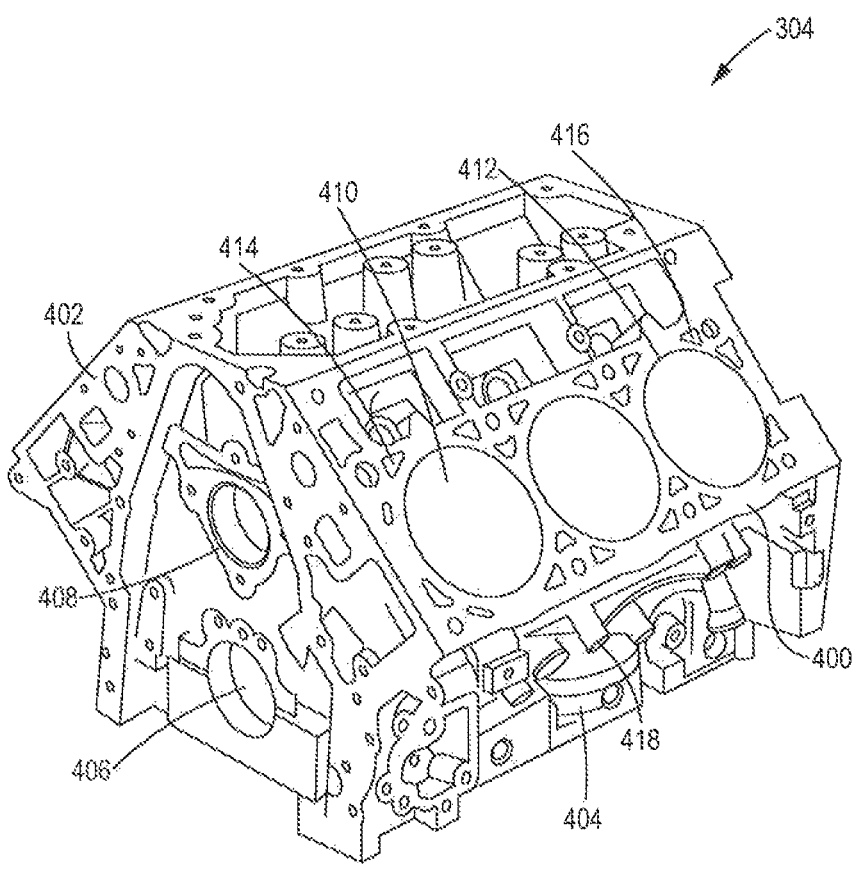
FIG. 5 is a perspective view of a crankcase, according to an embodiment of the present disclosure.

Now referring to FIG. 5, FIG. 5 illustrates the crankcase 304, according to one embodiment of the disclosure. The crankcase 304 may be provided for the cylinder head 300 having a right bank 400 and a left bank 402 designed to accommodate multiple cylinders arranged in a specific configuration. The crankcase 304 further includes block mounts 404, a crankshaft housing 406, a camshaft housing 408, a cylinder bore 410, a cylinder wall 412, a water jacket 414, a deck surface 416, water plugs 418, and.

The cylinder bore 410, enclosed by the cylinder wall 412, serves as the cylindrical chamber within which the reciprocating pistons operate. The pistons move back and forth within their respective cylinder bores, engaging with the combustion process that occurs in the combustion chambers 202. To maintain optimal operating temperatures, the crankcase 304 is equipped with a water jacket 414, which envelopes the crankcase 304, ensuring efficient circulation of coolant to dissipate heat generated during operation of the prime mover 106. The deck surface 416 provides a precisely machined and flat surface, ensuring a secure and hermetic connection between the cylinder head 300 and the engine block 200, sealing the combustion chambers 202 effectively.

The right bank 400 and the left bank 402 work harmoniously, facilitating the movement and timing of pistons, enabling the engine to convert thermal energy from combustion into mechanical work, ultimately driving the ground engaging elements 104. The camshaft housed within the camshaft housing 408 regulates the precise timing of intake and exhaust processes, ensuring optimal engine performance.

Figure 6:
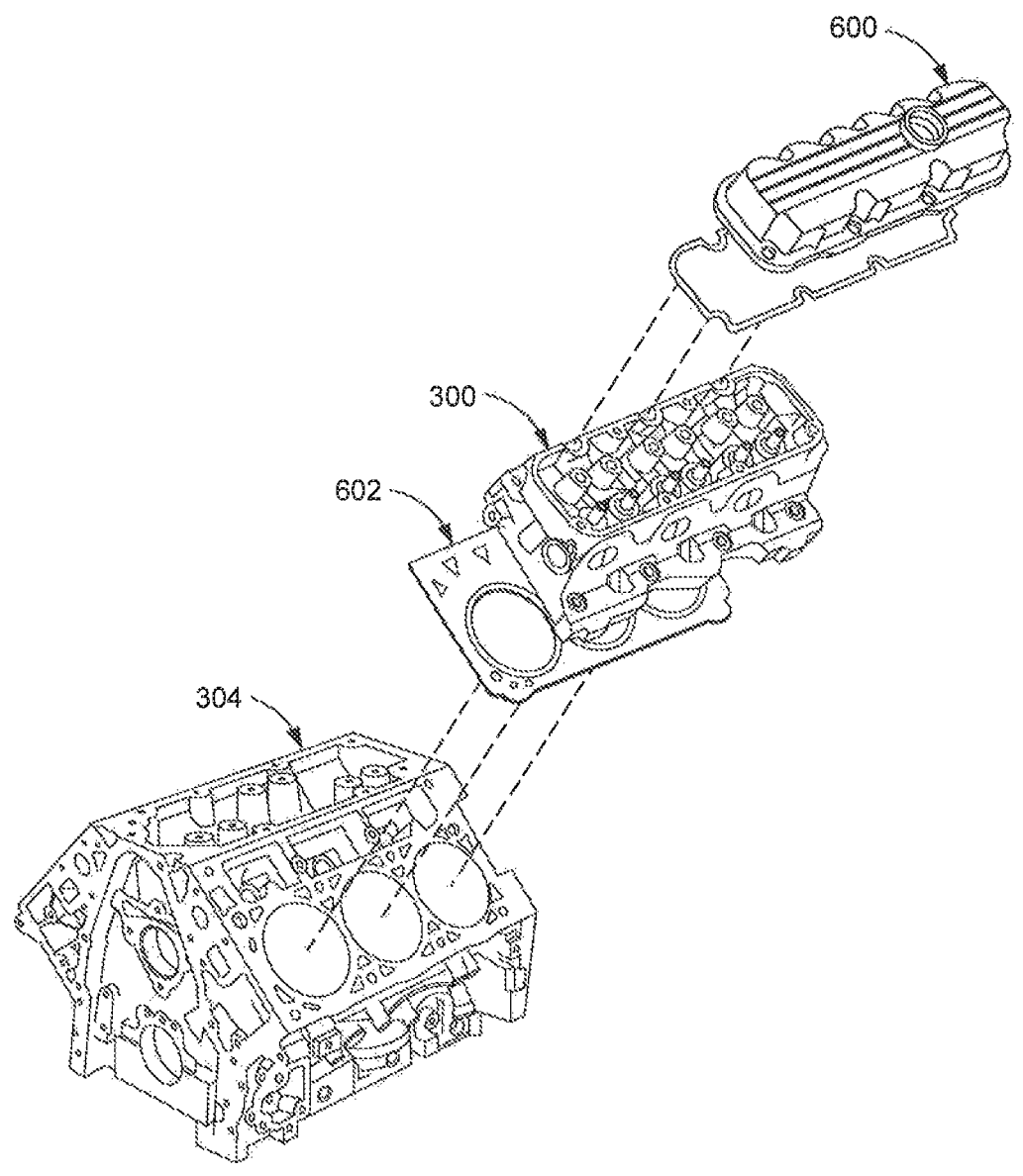
FIG. 6 is an exploded perspective view of a cylinder head mounted on the crank case of FIG. 5, according to an embodiment of the present disclosure.

Now referring to FIG. 6, the cylinder head 300 is shown in an exploded perspective view connected to the crankcase 304, according to an embodiment of the disclosure. The crankcase 304 may be configured to connect to more than one cylinder head 300 provided on the right bank 400 and the left bank 402. The cylinder head 300 may include engine valve cover 600, a bracket 602, and may further include valve seals, valve springs, and other essential components such as camshafts, lifters, and pushrods. These cylinder head components work together to manage the intake and exhaust of air and fuel, ensuring efficient combustion and overall engine performance. The engine valve cover 600 helps protect the valve train components, while the bracket 602 provides structural support. Valve seals and valve springs play crucial roles in maintaining proper valve operation, controlling oil flow, and regulating valve movement for optimal engine function.

Figure 7:
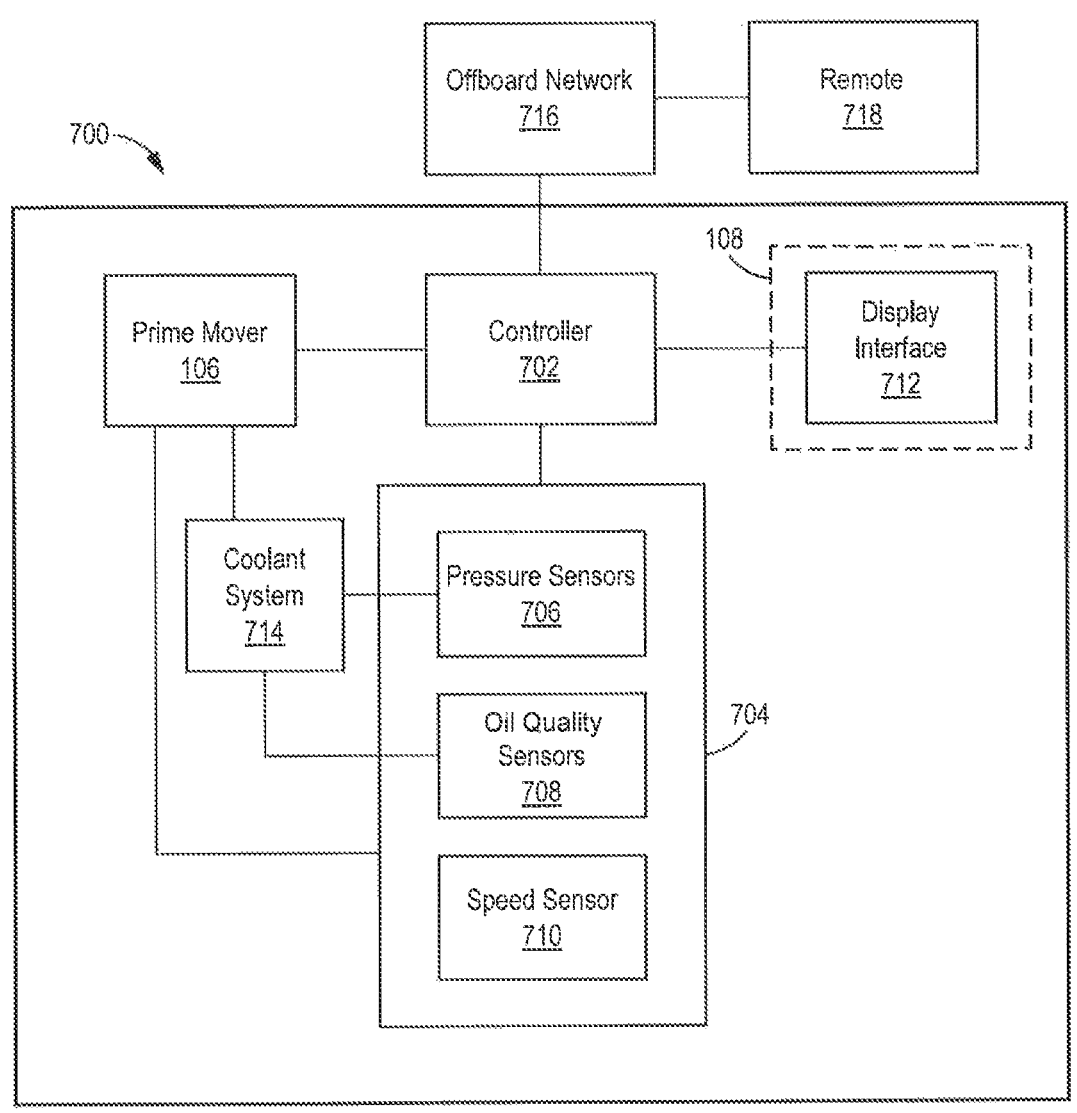
FIG. 7 is a schematic diagram of a cylinder head crack detection system, according to one embodiment of the disclosure.

Now referring to FIG. 7, a crack detection system 700 for detecting cracks in the cylinder head 300 is illustrated, according to an embodiment of the disclosure. The crack detection system 700 allows for early detection and classification of such cracks in the cylinder head 300 to prevent severe damage to the prime mover 106 ensuring its safe and reliable operation throughout its service life. When the crankcase 304 accommodates multiple cylinder heads, the crack detection system 700 detect cracks and determine the location of the crack whether in the cylinder head 300 on the right bank 400 or left bank 402. The crack detection system 700 includes the prime mover 106, a controller 702, and a sensor assembly 704 having a pressure sensor 706, an oil quality sensor 708, and a speed sensor 710. The controller may also be in communication with a display interface 712. The controller 702 may be in communication with a coolant system 714 associated with the water jacket 414 of the cylinder head 300 which may also be in communication with the pressure sensor 706 which may monitor the coolant pressure in the coolant system 714. The coolant system 714 may be a closed-loop feedback coolant system, as generally known in the arts.

The controller 702 may be further connected to an off-board network 716, allowing for the deployment of software updates and enhancements to improve the performance of the crack detection system 700 over time. To facilitate remote-control and oversight, operators may utilize a remote 718 to communicate with the controller 702 through the off-board network 716. The remote 718 enables operators to control, activate, or deactivate specific operational systems promptly in response to potential crack alerts, ensuring continued safe operation of the locomotive 100.

The crack detection system 700 may enable early detection and classification of cracks within the cylinder head 300. The crack detection system 700 comprises the prime mover 106, which includes the engine block 200 and the cylinder head 300. The prime mover 106 undergoes cyclic thermal and mechanical stresses during its operation, making it susceptible to crack formation. The crack detection system 700 includes a controller 702 that is component responsible for processing data and coordinating crack detection operations. The controller 702 interfaces with the sensor assembly 704, which includes the pressure sensor 706, the oil quality sensor 708, and the speed sensor 710.

The pressure sensor 706 may be provided to monitor the pressure variations within the combustion chambers 202 during operation. An increase or fluctuation in pressure levels can indicate the presence of cracks, and the pressure sensor 706 efficiently captures this critical data. Pressure sensors used in the prime mover 106 may include various types to suit specific needs, such as mechanical pressure sensors, piezoelectric pressure sensors, or MEMS-based sensors, ensuring precise and timely detection of any anomalies within the combustion chambers, as well as, water coolant pressure sensors for the coolant system 714, such as mechanical, piezoelectric, or capacitive sensors, as generally known in the arts. These water coolant pressure sensors can come in various types, including, each tailored to monitor the pressure of the engine's coolant system.

The oil quality sensor 608 monitors the changes in quality content of the oil in the engine block 200, such as monitoring the existing of elevated contents of sodium and/or water. The controller 702 processes signals received from the oil quality sensor 708, which may be connected to the oil pan 306, to ascertain whether the sodium content exceeds a Na (sodium) threshold in the engine lube oil or oil in the oil pan 306 by the oil quality sensor 708. The sodium is initially present in the coolant source, and when a crack occurs, a leak may result, causing the coolant to enter the combustion chambers 202 and then into the oil pan 306. Detecting the sodium content above the Na threshold can indicate the presence of coolant leakage due to cracks in the cylinder head 300, enabling timely and accurate identification. Oil lab analysis dataset may be automatically updated via the off-board network 716 and controller 702 for efficient detection of oil quality by the oil quality sensor 708. Additionally, oil samples may be taken from the oil pan 306 to be taken to a lab for periodic testing for the existence of sodium or water in the oil, which indicates the presence of coolant leakage indicative of cracks in the cylinder head 300.

The oil quality sensor 708 may employ physical and chemical measurements, monitoring parameters like viscosity, temperature, pressure, and contamination levels. Oil quality sensor 708 may be viscosity sensors, contamination sensors, dielectric sensors, or other chemical sensors as generally known in the art. These sensors may detect viscosity changes, impurities, and harmful water presence. These sensors may communicate with the controller 702, such as Engine Control Units (ECUs), to trigger alerts or automated maintenance actions when problems arise to ensures timely maintenance, prevents catastrophic failures, and optimize engine performance by scheduling oil changes based on real-time data.

To track the piston 302 movement and engine speed, the speed sensor 710 is incorporated. Anomalies in the piston 302's movement or engine speed may be indicative of cracks in the cylinder head 300 affecting the piston 302's operation. The speed sensor 710 may measure the rotational speed of the crankshaft, tracking the engine's operating speed such as in revolutions per minute (RPM).

The sensor assembly 704 collaborates with the controller 702, which processes the sensor data to identify potential cracks and determine their classification or location within the cylinder head 300. The controller 702 processes various parameters, coolant pressure feedback, engine duty cycle, and oil lab analysis data, to detect the existence of cracks and alert an operator of the crack and its location in the cylinder head 300.

The controller 702 in the locomotive 100 may control one or more operational systems associated with the locomotive 100. The operational systems may be one of many operating systems found within a locomotive 100 such as an ignition system, a fuel injection system, an oil transport system, a transmission, a throttle system, a power system, a braking system, a cooling system, a navigation system, a lighting system, an alarm system, a battery system, and/or an engine or other propulsion system, as generally known in the arts. These systems may also include one or more hydraulic, mechanical, electronic, and software-based components in which the controller 702 may communicate with and control, as generally known in the arts.

The controller 702 may be in communication with the coolant system 714 associated with the water jacket 414 of the crankcase 304. This communication allows the controller 702 to monitor coolant pressure and temperature, via the sensor assembly 704, providing valuable data for the crack detection algorithm. As the engine operates and the coolant circulates through the water jacket 414, any coolant loss resulting from cracks in the cylinder head 300 may lead to changes in coolant pressure and temperature. By analyzing these variations, the controller 702 can identify potential crack formations and their locations, facilitating early detection and classification of cracks in the cylinder head 300.

The continuous operation-cycles of the prime mover 106 subjects the cylinder head 300 to cyclic thermal and mechanical stresses. These variations in temperature and pressure over time can lead to fatigue damage, causing the material of the cylinder head 300 to weaken and develop cracks. The presence of cracks in the cylinder head 300 can compromise the seal it provides for the combustion chambers 202. When the seal is compromised, there is a risk of gas leaks and loss of pressure, which can reduce efficiency of the prime mover 106 and potentially lead to malfunctions. The formation of cracks in the cylinder head 300 can adversely affect this process, hindering the smooth movement of the piston 302 and impacting the overall performance of the prime mover 106. Moreover, when the presence of cracks in the cylinder head 300 can compromise the seal resulting in coolant from the coolant system 714 entering the combustion chambers 202 or engine block 200. Liquid coolants may contain sodium, as generally known in the arts, which may leak into the combustion chambers 202 or engine block 200 upon occurrence of cracks in the cylinder head 300.

Instances of cracks occurring in the cylinder head 300 are often related to the operating conditions in which the locomotive 100 is exposed. High-pressure and high-temperature environments within the combustion chambers 202 can subject the cylinder head 300 to significant stress and thermal gradients, leading to fatigue damage cycles over time. As the prime mover 106 undergoes repeated duty cycles, with frequent starts, stops, and varying loads, the cyclic stress can further exacerbate the development of cracks in the cylinder head 300. The combination of continuous thermal cycling, pressure fluctuations, and mechanical stress in locomotive engines can cause localized weakening of the material comprising the cylinder head 300, resulting in crack formation. Early detection and classification of these cracks is crucial to prevent catastrophic engine failure and ensuring the safe and reliable operation of the locomotive 100 throughout its service life.

Calculations conducted by the controller 702, based on signals received from the sensor assembly 704, can be conducted by a cloud based architecture, or local network architecture, as part of a hybrid or automated cylinder head crack detection methodology, as disclosed herein. Calculations can also be conducted in a non-automated manner via a local computer using data provided from the sensor assembly 704 of the prime mover 106 for identifying and classifying cracks in the cylinder head 300, e.g. in a repair facility. Additional data may be uploaded to the cloud-based architecture connected to the controller 702 from a customer facility, or a back-office network, as generally known in the arts. For example, a customer may upload period data samples of oil samples removed from the oil pan 306 which may be provided to the controller 702 for real-time analysis.

INDUSTRIAL APPLICABILITY

In operation, the present disclosure may find applicability in many industries including, but not limited to, the train, automotive, construction, earth-moving, mining, and agricultural industries. Specifically, the systems, machines, and methods of the present disclosure may be used for detecting cracks in cylinder heads of locomotive engines during operation of locomotives including, but not limited to, trains, boats, excavators, backhoes, rope shovels, skid steers, wheel loaders, tractors, and similar locomotives utilizing combustion engines. While the foregoing detailed description is made with specific reference to trains, it is to be understood that its teachings may also be applied onto the other machines such as boats, excavators, trucks, draglines, skid steers, rope shovels, wheel loaders, and the like. The crack detection system 700 may be provided as a retrofit onto these other applications that require detection of cylinder head cracks, particularly in locomotive engines subjected to high thermal gradients and pressure loads.

The challenging operating conditions expose cylinder heads to cyclic thermal stress and pressure fluctuations, leading to fatigue damage cycles and the development of cracks in the cylinder head 300. Early detection of these cracks is vital to prevent severe engine damage, as cracks may lead to seal failure, engine malfunction, and potential catastrophic failures. By incorporating the crack detection system 700, operators may ensure safe and reliable engine operation, minimize downtime, and optimize overall performance throughout the locomotive 100's service life. The ability of the crack detection system 700 to promptly identify and classify cracks in the cylinder head 300 enabling operators to take necessary preventive measures and efficiently address potential issues, early utilization of a limp-home mode feature of the prime mover 106, and ensuring the continued functionality and safety of the locomotive 100.

Cylinder heads, such as the cylinder head 300 depicted in FIG. 5, seals the combustion chambers 202 and enables the conversion of thermal energy into mechanical work. However, the demanding operating conditions, characterized by cyclic thermal stress and pressure fluctuations, can lead to fatigue damage cycles and the development of cracks in the cylinder head 300 and/or the material comprising the cylinder head 300. Such cracks can be detrimental in the cylinder head 300, making early detection essential to prevent severe damage to the prime mover 106 and significant down-time of the locomotive 100. By utilizing the crack detection system 700, locomotive operators can ensure the safe and reliable operation of their engines, mitigating the risk of catastrophic failure and optimizing the locomotive 100's performance throughout its service life.

Figure 8:
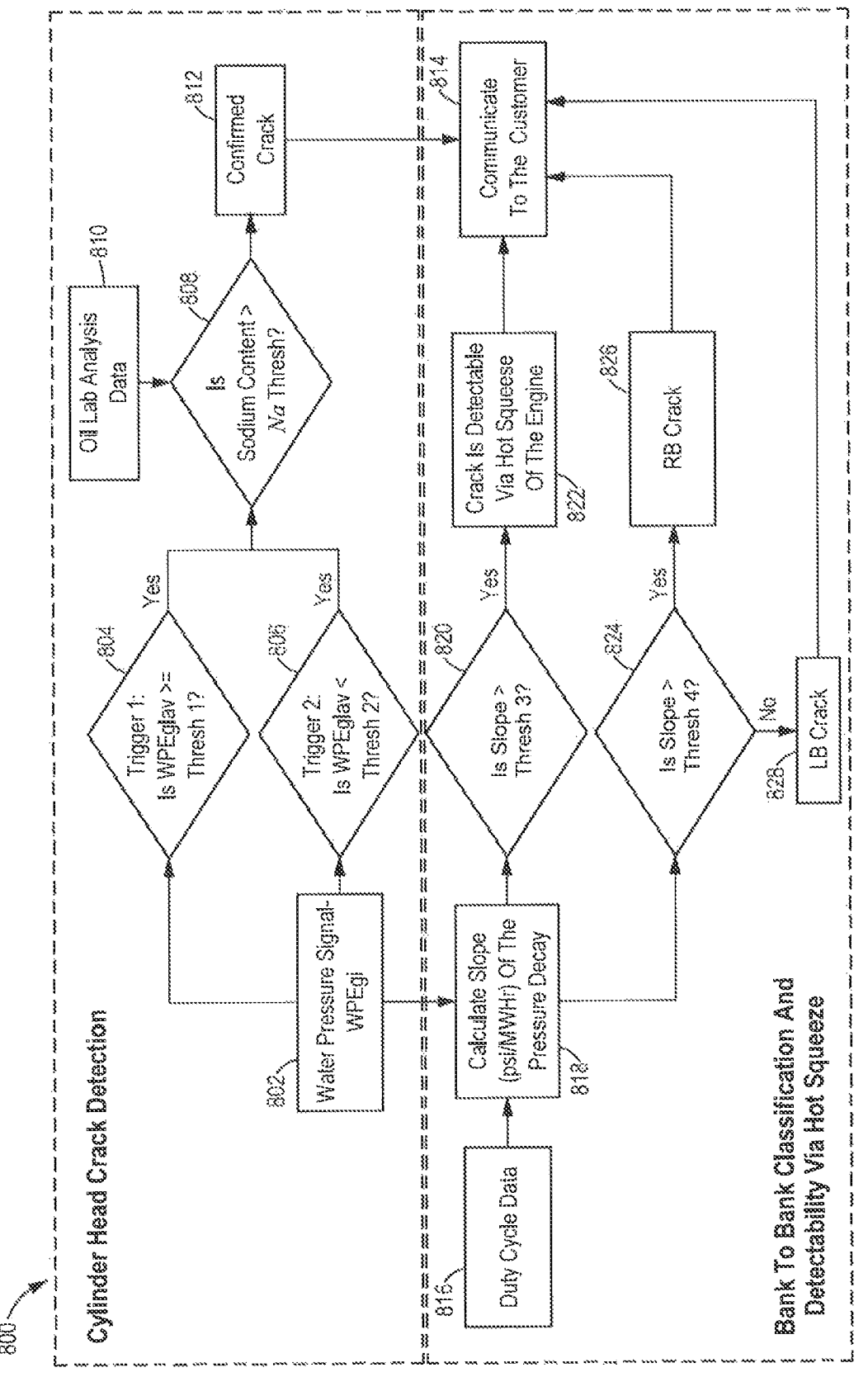
FIG. 8 is a flow-chart of an operation of the cylinder head crack detection system of FIG. 6, according to an embodiment of the present disclosure.

Now referring to FIG. 8, an operation 800 of the crack detection system 700 of FIG. 7 is illustrated, according to an embodiment of the present disclosure. In an operation 802, the pressure sensor 706 communicates to the controller 702 coolant pressure signals. The controller 702 processes the coolant pressure signal and determines whether the coolant pressure signals are greater then and/or equal to a first threshold, in an operation 804, and less than and/or equal to a second threshold, in an operation 806. The first threshold and second threshold ranges identify potential coolant leaks and for detecting deviations from normal operating conditions, indicating possible cracks in the cylinder head 300.

In operation 808, the controller 702 processes signals received to ascertain whether the sodium content exceeds a Na (sodium) threshold in the engine lube oil or oil in the oil pan 306 by the oil quality sensor 708. The sodium is initially present in the coolant source, and when a crack occurs, a leak may result, causing the coolant to enter the combustion chambers 202 and then into the oil pan 306. Detecting the sodium content above the Na threshold can indicate the presence of coolant leakage due to cracks in the cylinder head 300, enabling timely and accurate identification. In an operation 810, an oil lab analysis dataset may be automatically updated via the off-board network 716 and controller 702. The oil quality sensor 708 may be configured to detect a water and/or sodium content in the oil and issue an alert signal when the presence of water exceeds an allowable H20 threshold in the oil. Alternatively, in operation 820, in lieu of the oil quality sensor 708, oil samples may be taken from the oil pan 306 to be taken to a lab for periodic testing to detect the existence of sodium or water in the oil, which indicates the presence of coolant leakage indicative of cracks in the cylinder head 300. Oil sample may be taken before and after every work shift, or as generally known in the arts.

In an operation 812, the controller 702 confirms the crack exist in the cylinder head 300. In an operation 814, the controller 702 communicates to the display interface 712 to alert the operator of the locomotive 100.

In an operation 816, the controller 702 processes a duty cycle data of the prime mover 106 from signals received from the sensor assembly 704. When a crack occurs, the pressure begins to drop due to leakage of coolant. A slope of the pressure drop decay is calculated from the duty cycle data, in an operation 818. In an operation 820, the controller 702 processes signals received to ascertain whether the slope exceeds a third threshold, which is a speed dependent threshold. In an operation 822, a crack is detectable via a "hot squeeze" of the prime mover 106. A hot squeeze occurs when additional air pressure is provided in the coolant system 714 forcing coolant leakage out of the locations where the crack exists in the cylinder head 300. The controller 702 then communicates to the display interface 712 to alert the operator of the locomotive 100, in operation 814.

The calculations of the first threshold in operation 804, the second threshold in operation 806, the pressure decay in operation 818, the third threshold in operation 820, and the fourth threshold in operation 822 are all speed dependent and the calculations may be conducted continuously at every given speed during operation. The controller 702 dynamically and continuously calculates the pressure decay and the first, second, third, and fourth thresholds from signals received by the sensor assembly 704, pressure sensor 706, and speed sensor 710. The calculations are continuously completed for a given engine speed (throttle) and the controller 702 uses the calculated threshold for the provided speed as the third threshold. The pressure in the coolant system 714 may be produced by a coolant pump. The coolant pump may be connected to the engine and be dependent on engine speed at a given moment or the coolant pump may be provided independent of the engine whereby it has its own power supply, as generally known in the arts. The thresholds may also not be dependent on engine speed when an independent coolant pump is utilized and the thresholds may be based on various engine operating parameters and/or predetermined parameters.

In an operation 824, the controller 702 processes signals received to ascertain whether the slope exceeds a fourth threshold, which may be based on speed signals received from the speed sensor 710 and communicated to the controller 702. If the slope exceeds the fourth threshold, then the controller 702 will process that the crack is located in the right bank 400, in an operation 826. If the slope is less than the fourth threshold, then the controller 702 will process that the crack to be located in the left bank 402, in an operation 828.

Now referring to FIG. 9, a method 900 for detecting cracks in the cylinder head 300 of the locomotive 100 is illustrated, according to one embodiment. In a step 902, the locomotive 100 is provided with the frame 102, the ground engaging elements 104 supporting the frame 102, the prime mover 106 mounted within the frame 102, and the controller 702. Additionally, the locomotive 100 is provided with the coolant system 714 for efficiently cooling the cylinder head 300 and the sensor assembly 704 in communication with the controller 702. The sensor assembly 704 may include one or more of the pressure sensor 706, the oil quality sensor 708, and the speed sensor 710. The coolant system 714 may be provided as a closed-loop system.

In a step 904, the prime mover 106 is activated and begins operation, powering the locomotive 100 and facilitating its movement. During operation, in a step 906, the coolant system 714 cools the cylinder head 300 to actively maintain the temperature of the cylinder head 300 in a closed-loop system, minimizing overheating to inhibit cracks. The coolant pressure feedback of the coolant in the coolant system 714 is monitored by the pressure sensor 706.

In a step 908, the sensor assembly 704, in communication with the controller 702, continuously monitors the coolant pressure of the coolant system 714, oil quality, and the engine duty cycle, as the prime mover 106 operates. The sodium content may also be monitored in the engine block 200 and the combustion chambers 202 for coolant leakage, as the prime mover 106 operates.

In a step 910, the controller 702 identifies existence of a crack in the cylinder head 300 from input signals received from the sensor assembly 704 when the coolant pressure signals are greater than or equal to the first threshold and less than the second threshold. The first threshold and the second threshold may be configured to by varying levels of pressure are triggered by signals received by the controller 702 from the pressure sensor 706. These thresholds may be dynamically configured to respond to varying levels of pressure, with their activation governed by signals received by the controller 702 from the pressure sensor 706.

In a step 912, the controller 702 classifies the location of the cracks in the right bank 400 of the cylinder head when the controller 702 calculates a pressure decay, via the pressure sensor 706, greater than the third threshold and greater than the fourth threshold.

In a step 914, the controller 702 classifies the location of the cracks in the left bank 402 of the cylinder head when the controller 702 calculates a pressure decay, via the pressure sensor 706, greater than the third threshold and less than the fourth threshold.

In a step 916, the controller 702 alerts the existence of the crack to an operator of the locomotive 100, via communicating an alert signal. The controller 702 may communicate the alert signal to the display interface 712.

Upon the identification of a crack, the controller 702 may activate a limp-home mode feature to enable the prime mover 106 to operate at reduced performance levels reach a safe location or repair facility. During this mode, the power of the prime mover 106 may be limited to prevent additional damage to the prime mover 106.

From the foregoing, it can be seen that the technology disclosed herein has industrial applicability in the fields of locomotives for ensuring early detection of cracks in the cylinder heads of locomotive engines for early detection of damaged components, reducing down-time of the locomotive, and improving service time.

What is claimed is:

1. A crack detection system for a cylinder head associated with an internal combustion engine of a locomotive, comprising:
   a closed-loop coolant system for cooling the cylinder head;
   a sensor assembly including a pressure sensor, and a speed sensor; and
   a controller in communication with the sensor assembly and configured to monitor a coolant pressure feedback, and an engine duty cycle of the internal combustion engine,
   the controller further configured to communicate an alert signal indicative of an existence of a crack in the cylinder head when:
      coolant pressure signals are greater than or equal to a first threshold and less than a second threshold; and
      a pressure decay is calculated greater than a third threshold.

2. The crack detection system of claim 1, wherein the cylinder head is a multi-bank cylinder head and the controller is configured to classify a location of the crack in a right bank of the cylinder head when the controller calculates the pressure decay to be greater than the third threshold and greater than a fourth threshold.

3. The crack detection system of claim 2, wherein the controller is configured to classify the location of the crack in a left bank of the cylinder head when the controller calculates the pressure decay to be greater than the third threshold and less than the fourth threshold.

4. The crack detection system of claim 1, further comprising an oil quality sensor,
   wherein the controller is configured to communicate the alert signal when the controller receives signals from the oil quality sensor indicative of a sodium content or a water content above an impurity threshold in an oil in the internal combustion engine.

5. The crack detection system of claim 1,
   wherein the controller is configured to communicate the alert signal to a display interface in a cab of the locomotive, and
   wherein the controller is further configured to activate a limp-home mode feature upon detection of existence of cracks in the cylinder head.

6. The crack detection system of claim 1, the controller is further connected to an off-board network and a remote, whereby the off-board network is a cloud based architecture for online remote monitoring and for updating oil quality data.

7. The crack detection system of claim 1, wherein a crack is detectable via hot squeeze if the pressure decay is greater than the third threshold.

8. A locomotive comprising:
   a frame;
   a prime mover mounted on the frame;
   a ground engaging element supporting the frame;
   a cab; and
   a crack detection system for a cylinder head associated with the prime mover, including:
      a closed-loop coolant system for cooling the cylinder head;
      a sensor assembly including a pressure sensor, an oil quality sensor, and a speed sensor; and
      a controller in communication with the sensor assembly and configured to monitor a coolant pressure feedback, an engine duty cycle of the prime mover, and a sodium content in the prime mover,
      the controller further configured to communicate an alert signal indicative of an existence of a crack in the cylinder head detected when:
         coolant pressure signals are greater than or equal to a first threshold and less than a second threshold; and
         a pressure decay is calculated greater than a third threshold.

9. The locomotive of claim 8, wherein the cylinder head is a multi-bank cylinder head and the controller classifies a location of the crack in a right bank of the cylinder head when the controller calculates the pressure decay to be greater than the third threshold and greater than a fourth threshold.

10. The locomotive of claim 9, wherein the controller is configured to classify the location of the crack in a left bank of the cylinder head when the controller calculates the pressure decay to be greater than the third threshold and less than the fourth threshold.

11. The locomotive of claim 8, wherein the controller is further configured to communicate the alert signal when the controller receives signals from the oil quality sensor indicative of a sodium content is above a Na threshold in an oil in the prime mover.

12. The locomotive of claim 8, wherein the controller is configured to communicate the alert signal to a display interface in the cab of the locomotive.

13. The locomotive of claim 8, wherein the controller is further configured to activate a limp-home mode feature upon detection of existence of cracks in the cylinder head.

14. The locomotive of claim 8, wherein the controller is further connected to an off-board network and a remote, whereby the off-board network is a cloud based architecture for online remote monitoring and for updating oil quality data.

15. The locomotive of claim 8, wherein a crack is detectable via hot squeeze if the pressure decay is greater than the third threshold.

16. A method for detecting and classifying cracks in a cylinder head of a prime mover in a locomotive, the method comprising:

providing a frame, a ground engaging element supporting the frame, the prime mover mounted in the frame, a controller, a closed-loop coolant system associated with the cylinder head, a sensor assembly in communication with the controller, the sensor assembly including a pressure sensor and a speed sensor;

operating the prime mover;

cooling the cylinder head using the closed-loop coolant system and monitoring a coolant pressure feedback via the pressure sensor;

monitoring, via the controller receiving signals from the sensor assembly, continuously for coolant pressure signals, and an engine duty cycle of the prime mover;

identifying existence of cracks in the cylinder head from signals received by the controller when the coolant pressure signals are greater than or equal to a first threshold and less than a second threshold;

classifying a location of the cracks in a right bank of the cylinder head when the controller calculates a pressure decay, via the pressure sensor, greater than a third threshold and greater than a fourth threshold;

classifying the location of the cracks in a left bank of the cylinder head when the controller calculates the pressure decay, via the pressure sensor, greater than the third threshold and less than the fourth threshold; and alerting existence of cracks to an operator of the locomotive, via communicating an alert signal by the controller.

17. The method of claim 16, further comprising:

identifying existence of cracks in the cylinder head from signals, received by the controller from an oil quality sensor for monitoring oil quality, indicative of a sodium content in an oil in a combustion chamber associated with the prime mover that is above an impurity threshold.

18. The method of claim 16, further comprising:

connecting the controller to an off-board network and a remote, whereby the off-board network is a cloud based architecture for online remote monitoring and for updating oil quality data; and communicating the alert signal and location of the cracks to a display interface in the locomotive.

19. The method of claim 16, further comprising:

removing samples of oil from an oil pan;

testing the samples of oil for a sodium content or a water content in the oil; and identifying existence of cracks in the cylinder head when the sodium content or the water content in the oil is above an impurity threshold.

20. The method of claim 18, further comprising:

communicating sample data, from periodic samples of oil, to the off-board network to update the controller.

* * * * *